(12) United States Patent
Fukuda et al.

(10) Patent No.: US 11,638,732 B2
(45) Date of Patent: May 2, 2023

(54) COMPOSITION FOR REDUCING DETERIORATION OF MENTAL FUNCTION

(71) Applicant: KIRIN HOLDINGS KABUSHIKI KAISHA, Tokyo (JP)

(72) Inventors: Takafumi Fukuda, Tokyo (JP); Yasuhisa Ano, Tokyo (JP)

(73) Assignee: KIRIN HOLDINGS KABUSHIKI KAISHA, Tokyo (JP)

(*) Notice: Subject to any disclaimer, the term of this patent is extended or adjusted under 35 U.S.C. 154(b) by 66 days.

(21) Appl. No.: 17/040,379

(22) PCT Filed: Nov. 12, 2018

(86) PCT No.: PCT/JP2018/041809
§ 371 (c)(1),
(2) Date: Sep. 22, 2020

(87) PCT Pub. No.: WO2019/181058
PCT Pub. Date: Sep. 26, 2019

(65) Prior Publication Data
US 2021/0060107 A1 Mar. 4, 2021

(30) Foreign Application Priority Data
Mar. 23, 2018 (JP) .............................. JP2018-055948

(51) Int. Cl.
*A61K 36/185* (2006.01)
*A23L 33/105* (2016.01)
*A61P 25/22* (2006.01)
*A61P 25/24* (2006.01)
*A61K 9/00* (2006.01)

(52) U.S. Cl.
CPC .......... *A61K 36/185* (2013.01); *A23L 33/105* (2016.08); *A61P 25/22* (2018.01); *A61P 25/24* (2018.01); *A61K 9/0053* (2013.01)

(58) Field of Classification Search
None
See application file for complete search history.

(56) References Cited

U.S. PATENT DOCUMENTS

| | | | | |
|---|---|---|---|---|
| 2013/0316023 A1* | 11/2013 | Manabe | ..................... | A61P 3/06 424/725 |
| 2017/0037345 A1 | 2/2017 | Taniguchi et al. | | |
| 2019/0117715 A1 | 4/2019 | Kanayama et al. | | |

FOREIGN PATENT DOCUMENTS

| | | | |
|---|---|---|---|
| DE | 102009023549 A1 | 12/2010 | |
| EP | 2865744 A1 | 4/2015 | |
| JP | 2006-213628 A | 8/2006 | |
| KR | 10-2016-0011756 A | 2/2016 | |
| WO | 2012/081675 A1 | 6/2012 | |
| WO | 2017/179354 A1 | 10/2017 | |

OTHER PUBLICATIONS

Hryhorczuk et al. (2013) Frontiers in Neuroscience, vol. 7, Article 177 (14 pages). (Year: 2013).*
Kyrou et al. (2017) Hormones 16(2): 171-180. (Year: 2017).*
Rosmond (2004) Medical Hypotheses 62,, 976-979. (Year: 2004).*
Raskin et al. (2004) Current Pharmaceutical Design, 10, 3419-3429. (Year: 2004).*
Revilla et al. (1998) J. Agric. Food Chem. 46,, 4592-4597. (Year: 1998).*
Akira Monji, "The Neuroinflammation Hypothesis of Psychiatric Disorders", Psychiatria et Neurologia Japonica, 2012, vol. 114, No. 2, pp. 124-133.
Hirifumi Kouda, "Anti-stress Effect of Beer Aroma Components", Journal of the Brewing Society of Japan, 2006, vol. 101, No. 12, pp. 927-934.
Giuseppina Negri et al., "Bitter acids from hydroethanolic extracts of *Humulus lupulus* L., Cannabaceac, used as anxiolytic", Revista Brasileira de Farmacognosia, Dec. 2010, vol. 20, No. 6, pp. 850-859.
Hajime Bab, "Relationship between Depression and Dementia: Risk and Partial Manifestation", Japanese Journal of Geriatric Psychiatry, Jan. 2018, vol. 29, No. 1, pp. 20-28.
International Search Report for PCT/JP2018/041809, dated Dec. 11, 2018 (PCT/ISA/210).
Extended European Search Report, dated Dec. 1, 2021, issued by the European Patent Office in European Patent Application No. 18911291.5.
Thomson Scientific, "Database WPI", Week 201623, AN 2016-10751V, XP002804436, 2 pages total.
Paola Zanoli et al., "Pharmacognostic and pharmacological profile of *Humulus lupulus* L.", Journal of Ethnopharmacology, 2008, vol. 116, pp. 383-396 (14 pages total).
Rocio Garcia-Villalba et al. "Analysis of Hop Acids and Their Oxidized Derivatives and Iso-α-acids in Beer by Capillary Electrophoresis-Electrospray Ionization Mass Spectrometry", J. Agric. Food Chem, 2006, vol. 54, pp. 5400-5409 (10 pages total).

* cited by examiner

*Primary Examiner* — Russell G Fiebig
(74) *Attorney, Agent, or Firm* — Sughrue Mion, PLLC

(57) ABSTRACT

An object of the present invention is to provide a novel composition that is, for example, effective in suppression of deterioration of mental function. The present invention provides a composition for use in suppressing deterioration of mental function, comprising a hop oxidation-reaction product. Conditions of deterioration of mental function include conditions selected from the group consisting of depression-related conditions and anxiety-related conditions. The composition of the present invention can be provided in the form of a food composition, and be ingested by subjects with deterioration of mental function or with a risk of deterioration of mental function. The S-fraction can be used as the hop oxidation-reaction product.

5 Claims, 3 Drawing Sheets

COMPOSITION FOR REDUCING DETERIORATION OF MENTAL FUNCTION

CROSS REFERENCE TO RELATED APPLICATIONS

This application is a National Stage of International Application No. PCT/JP2018/041809, filed Nov. 12, 2018, claiming priority based on Japanese Patent Application No. 2018-055948, filed Mar. 23, 2018.

TECHNICAL FIELD

The present invention relates to a composition, for example, for suppressing deterioration of mental function.

BACKGROUND ART

In modern society, people from a wide variety of generations, from young to old, suffer from chronic fatigue and/or stress on a daily basis. Chronic fatigue and stress may affect mental functions and lead to deterioration of mental function, such as loss in willingness and a symptom of depression. In recent studies, the involvement of brain inflammation in the mechanism is being elucidated (Non-Patent Document 1).

Hops are responsible for bitterness in beer and have a long history of use in folk medicine, and it is known that hops have various health benefits such as sedative and anti-indigestion effects. Hop extracts added to foods and beverages beyond a certain level cause a distinct and strong bitter taste and are likely to damage the palatability of the foods and beverages. However, it is reported that hops can reduce their characteristic bitter taste, while maintaining the lipid metabolism-improving function, upon oxidation-treatment (Patent Document 1). However, there is so far no report describing the relationship between hop-derived components or oxidation products thereof and mental functions.

REFERENCE LIST

Patent Document

Patent Document 1: WO2012/081675

Non-Patent Document

Non-Patent Document 1: Akira Monji, Psychiatria et Neurologia Japonica (2012) 114(2): 124-133

SUMMARY OF THE INVENTION

In this invention, the inventors found that a hop oxidation-reaction product was effective in alleviation of brain inflammation as well as in improvement of a depression condition and loss in willingness. The inventors also found that a hop oxidation-reaction product was effective in improvement of mood states and mental states in human. The present invention is based on these findings.

That is, an object of the present invention is to provide a novel composition that is, for example, effective in suppression of deterioration of mental function.

According to the present invention, the following inventions are provided.

[1] A composition or agent for use in suppressing deterioration of mental function, comprising a hop oxidation-reaction product.

[2] The composition or agent according to [1], wherein the deterioration of mental function includes one or more conditions selected from the group consisting of depression-related conditions and anxiety-related conditions.

[3] The composition or agent according to [1], wherein the deterioration of mental function is deterioration of a mood state or deterioration of a mental state.

[4] The composition or agent according to any one of [1] to [3], which is ingested by a subject with deterioration of mental function or with a risk of deterioration of mental function.

[5] The composition or agent according to any one of [1] to [4], wherein the deterioration of mental function is caused by stress or chronic fatigue.

[6] The composition or agent according to any one of [1] to [5], which is a food composition.

[7] The composition or agent according to any one of [1] to [6], which is in a single unit package suitable for a single ingestion.

[8] The composition or agent according to any one of [1] to [7], wherein the hop oxidation-reaction product is the S-fraction.

[9] The composition or agent according to [8], which comprises the S-fraction in an amount of 1 to 500 mg on the dry-mass basis for a single ingestion.

[10] A composition or agent for treating, preventing, or improving depression and/or anxiety, comprising a hop oxidation-reaction product.

In this specification, the compositions according to the above [1] and [10] and the agents according to the above [1] and [10] may be referred to as "the compositions of the present invention" and "the agents of the present invention," respectively.

By the present invention, a composition comprising a hop oxidation-reaction product that can exert functions such as suppression of deterioration of mental function is provided. The composition according to the present invention is advantageous in that it can be used as a functional material that is safe for mammals including human, because a component derived from hop, which humans have taken as a food for long years, is used for the hop oxidation-reaction product.

DETAILED DESCRIPTION OF THE INVENTION

Hop Oxidation-Reaction Product

Figure 1:
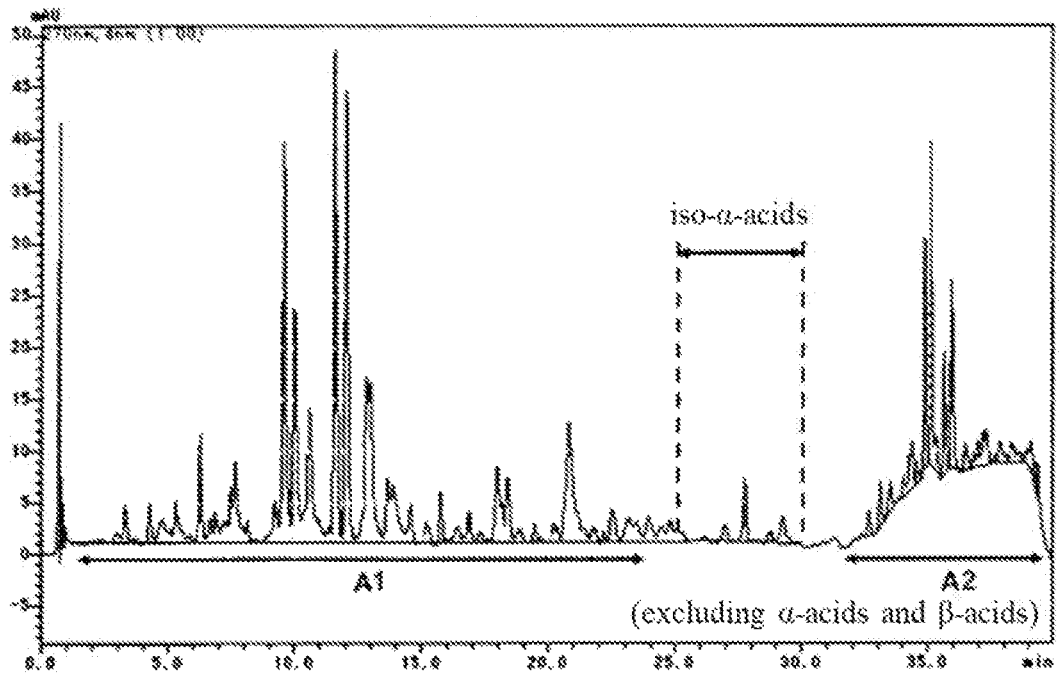
FIG. 1 is a figure showing the result of HPLC analysis (HPLC chromatogram) of a hop oxidation-reaction product in Reference Example 1.

In the present invention, hop oxidation-reaction products represent products obtained by subjecting hops or hop products (such as hop pellets and extracts) to oxidation. A hop oxidation-reaction product provided by the present invention can be obtained by, for example, bringing hops into contact with oxygen in the air and thereby oxidizing the hops.

Hop oxidation-reaction products can be produced by oxidizing hops according to, for example, the method described in Patent Document 1. Oxidation is preferably performed by heating hops in the air. The heating temperature is not specifically limited, but the upper limit of heating temperature is preferably 100° C., more preferably 80° C. A heating temperature of not higher than 100° C. is advantageous for progression of oxidization in preference to isomerization. Moreover, the lower limit of heating temperature is preferably 60° C. A heating temperature of not lower than 60° C. is advantageous for efficient progression of oxidation. Moreover, the reaction period is also not specifically limited, but can be appropriately determined depending on the variety of hop and the reaction temperature. For example, when the reaction temperature is at 60° C., a reaction period of 48-120 hours is preferred; when the reaction temperature is at 80° C., a reaction period of 8-24 hours is preferred. The form of hops to be subjected to oxidation is not specifically limited as long as they can be brought into contact with oxygen in the air, but the required reaction time can be shortened by processing hops, preferably into a powdery form.

In the present invention, hops may have any form as long as they contain lupulin, and harvested and undried hops, harvested and dried hops, compressed hops, ground hops, hops processed into a pellet form, or the like may be used. Among those, hop pellets are preferred. Commercially available hop pellets may be used, and include, for example, hop strobiles compressed into a pellet form (Type 90 pellet), pellets in which lupulin have been selectively concentrated (Type 45 pellet), or hop pellets subjected to isomerization treatment (for example, Isomerized Pellets (Hopsteiner)).

A hop extract oxidation-reaction product, which is generated by subjecting a hop extract to oxidation, may be provided as the hop oxidation-reaction product in the present invention. Hop extract oxidation-reaction products can be produced by oxidizing hop extracts according to, for example, the method described in Patent Document 1.

Hop contains acidic resin components, such as α-acids (humulones), β-acids (luplones), iso-α-acids (isohumulones) and the like. In the present invention, "humulones" is used to refer inclusively to humulone, adhumulone, cohumulone, posthumulone, and prehumulone. Moreover, in the present invention, "luplones" is used to refer inclusively to lupulone, adlupulone, colupulone, postlupulone, and prelupulone. Furthermore, in the present invention, "isohumulones" is used to refer inclusively to isohumulone, isoadhumulone, isocohumulone, isoposthumulone, isoprehumulone, Rho-isohumulone, Rho-isoadhumulone, Rho-isocohumulone, Rho-isoposthumulone, Rho-isoprehumulone, tetrahydroisohumulone, tetrahydroisoadhumulone, tetrahydroisocohumulone, tetrahydroisoprehumulone, tetrahydroisoposthumulone, hexahydroisohumulone, hexahydroisoadhumulone, hexahydroisocohumulone, hexahydroisoposthumulone, and hexahydroisoprehumulone. In addition, isohumulones include cis- and trans-stereoisomers, and "isohumulones" is used to refer inclusively to both stereoisomers, unless otherwise specifically stated.

By subjecting hops to oxidation, the contents of α-acids, β-acids and iso-α-acids are decreased, and the contents of components other than those acids are increased. Examples of such hop oxidation-reaction products include, among hop oxidation-reaction products, hop oxidation-reaction products showing peaks of α-acids, β-acids and iso-α-acids with an area equal to 20% or lower, preferably 10% or lower, of the total area of all HPLC peaks, in cases where HPLC analysis similar to that in Example 1 is performed.

In addition to α-acids, β-acids and iso-α-acids, other components contained in an oxidation product according to the present invention can be readily detected by well-known analytical techniques, such as HPLC. For example, a hop oxidation-reaction product prepared by a procedure similar to that described in Example 1 of Patent Document 1 contains other components in addition to α-acids, β-acids and iso-α-acids, and peaks corresponding to those other components (also referred to collectively as "S-fraction (S-Fr)" in this specification) can exhibit bioactivities. Peaks within the ranges indicated by arrows in FIG. 1A for Example 1 of Patent Document 1 (excluding the peaks of α-acids and β-acids) correspond to the S-fraction.

A HPLC analysis of a hop oxidation-reaction product prepared under the same conditions as those in Patent Document 1 and the result of the analysis (HPLC chromatogram) are as demonstrated in Reference Example 1 and FIG. 1. Peaks within the ranges indicated by Arrows A1 and A2 (excluding the peaks of α-acids and β-acids) correspond to the S-fraction. In FIG. 1, the total value of peak areas within the ranges indicated by Arrows A1 and A2 represents the sum of the values of peak areas within the range A1, which corresponds to the range of retention time from 3 minutes to 25 minutes, and the values of peak areas within the range A2 (excluding the peaks of α-acids and β-acids), which corresponds to the range of retention time from 32 minutes to 39 minutes. As used herein, the phrase "to a retention time of 25 minutes" in the range A1 means "to a time point when a peak identified as corresponding to trans-isocohumulone appears". Moreover, characteristic peaks were observed around a retention time of 9.7 minutes, a retention time of 11.8 minutes and a retention time of 12.3 minutes within the range indicated by A1 in FIG. 1. Furthermore, shoulder peaks were observed within the range indicated by A2 in FIG. 1, and the starting point was around a retention time of 32 minutes, the peak top points (excluding the peaks of α-acids and β-acids) were within the range of retention time from around 35 minutes to around 36 minutes, and the ending point was around a retention time of 39 minutes.

The hop oxidation-reaction product preferably contains oxidation products of α-acids, those of iso-α-acids, and those of β-acids, containing, for example, "tricyclooxyisohumulones" as such oxidation products. As used herein, the term "tricyclooxyisohumulones" refers to a group of compounds including tricyclooxyisocohumulone A (TCOIcoH A, see the following formula 1; IUPAC name: (3aS,5aS,7S,8aS)-3,3a-dihydroxy-7-(1-hydroxy-1-methylethyl)-6,6-dimethyl-2-(2-methylpropanoyl)-5a,6,7,8-tetrahydro-3aH,5H-cyclopenta[c]pentalene-1,4-dione), tricyclooxyisohumulone A (TCOIH A, see the following formula 2; IUPAC name: (3aS,5aS,7S,8aS)-3,3a-dihydroxy-7-(1-hydroxy-1-methylethyl)-6,6-dimethyl-2-(3-methylbutyryl)-5a,6,7,8-tetrahydro-3aH,5H-cyclopenta[c]pentalene-1,4-dione), and tricyclooxyisoadhumulone A (TCOIadH A, see the following formula 3; IUPAC name: (3aS,5aS,7S,8aS)-3,3a-dihydroxy-7-(1-hydroxy-1-methylethyl)-6,6-dimethyl-2-(2- methylbutanoyl)-5a,6,7,8-tetrahydro-3aH,5H-cyclopenta[c]pentalene-1,4-dione). In this specification, TCOIcoH A, TCOIH A and TCOIadH A may be hereinafter referred to collectively as TCOIHs A. The content of TCOIHs A is measured by a method as described in Example 1 below.

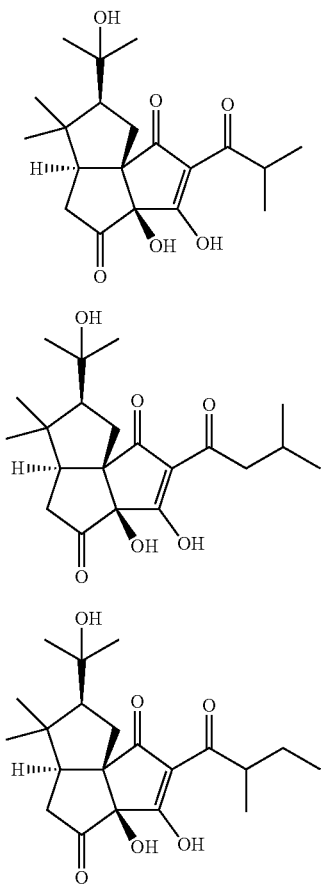

Formula 1

Formula 2

Formula 3

Oxidation products other than "tricyclooxyisohumulones" contained in the hop oxidation-reaction product (preferably in the S-fraction) include scorpio-humulinol A and scorpio-cohumulinol A.

In the present invention, the hop oxidation-reaction product may be provided as an extract in an aqueous medium. The aqueous medium is not specifically limited as long as it is commonly used for manufacturing a food, but the aqueous medium is preferably water or ethanol, more preferably water. Moreover, the extraction temperature is not specifically limited, but is preferably at 60° C. or lower and is more preferably in the range of 50-60° C. from the viewpoint of extraction efficiency.

The hop oxidation-reaction product used in the present invention (preferably, an extract of the hop oxidation-reaction product in an aqueous medium) can be characterized by the ratio of the total amount of tricyclooxyisohumulone A and tricyclooxyisocohumulone A to the total amount of scorpio-humulinol A and scorpio-cohumulinol A (on the dry-mass basis), and an extract of the hop oxidation-reaction product in an aqueous medium in which the above ratio ranges, for example, from 1 to 30, preferably from 2 to 20, can be used.

Also, the hop oxidation-reaction product used in the present invention can be characterized by the content ratio of TCOIHs contained in the S-fraction (on the dry-mass basis), and a hop oxidation-reaction product (preferably, an extract of a hop oxidation-reaction product in an aqueous medium) in which the above content ratio ranges, for example, from 5 to 15% by mass, preferably from 5 to 12% by mass, can be used. In cases where the S-fraction of a hop oxidation-reaction product comprises mainly the components in the fraction indicated by Arrow A1 in FIG. 1, the content of TCOIHs can be measured by a measurement method similar to that for matured hop bitter acids as described in Biosci. Biotechnol. Biochem., 2015 (79): 1684-1694.

The Brix value of an extract of the hop oxidation-reaction product in an aqueous medium is not specifically limited, but it is, for example, not higher than 3, and is preferably in the range of 1.5 to 3. Insoluble components in the extract of the hop oxidation-reaction product in an aqueous medium may be removed, for example, by decantation or with filter paper. The extract of the hop oxidation-reaction product in an aqueous medium may also be treated with activated charcoal.

The composition and agent according to the present invention may contain one or more other components intended for the prevention of deterioration of mental function, in addition to the hop oxidation-reaction product. Examples of the components intended for the prevention of deterioration of mental function include tryptophan.

Uses

As shown in Examples below, hop oxidation-reaction products (preferably, S-fraction) have effects to improve a depression condition and loss in willingness and to improve mood states and mental states and, furthermore, to alleviate brain inflammation. Since a depression condition, loss in willingness, deterioration of a mood state and deterioration of a mental state are representative examples of deterioration of mental function, and brain inflammation has been indicated to be involved in a depression condition and loss in willingness (Non-Patent Document 1), a hop oxidation-reaction product can be used as an active ingredient in compositions for use in suppressing deterioration of mental function and agents for suppressing deterioration of mental function.

In the present invention, the term "mental function" is used to refer inclusively to emotional functions (functions related to emotion and motivation) and mental vigor. The term "deterioration of mental function" is used to refer inclusively to deterioration of mental function caused by stress or chronic fatigue and to deterioration of mental function caused by brain inflammation. Examples of "deterioration of mental function" include, for example, depression-related conditions and anxiety-related conditions. Depression-related conditions include, for example, a depression condition, loss in willingness, loss in motivation, loss in spirit, loss in energy, feelings of despair, loneliness, dejection, hopelessness, and loss in interest. Anxiety-related conditions include, for example, feelings of uneasiness, mental fatigue, helplessness, restlessness, bewilderment, fear, and unnecessary anxiety. Examples of "deterioration of mental function" also include, for example, a depression condition, loss in willingness, deterioration of a mood state and deterioration of a mental state. Deterioration of a mood state and deterioration of a mental state includes, for example, deterioration of total mood disturbance, and the "total mood disturbance" means a mood state including anger-hostility, confusion-bewilderment, depression-dejection, fatigue-inertia, tension-anxiety, vigor-activity, and friendliness.

In the present invention, the phrase "suppressing deterioration of mental function" is used to refer inclusively to not only improvement of mental functions in subjects with deterioration of mental function, but also reduction of the risk of deterioration of mental function in subjects with a risk of deterioration of mental function. That is, the composition and agent according to the present invention can be ingested by or administered to subjects with deterioration of mental function or with a risk of deterioration of mental function. As used herein, the phrase "subject with a risk of deterioration of mental function" means a subject who currently shows no deterioration of mental function but has a risk of a future deterioration of mental function. Moreover, the phrase "reduction of the risk" includes alleviating deterioration of mental function. The subjects which the composition or the agent is ingested by or administered to are mammals including human, as described below.

As described above, a hop oxidation-reaction product can be used for the suppression of deterioration of mental function. Since deterioration of mental function is involved in development and progression of depression and anxiety conditions, a hop oxidation-reaction product can be used as an active ingredient in compositions and agents for treating, preventing, or improving depression and anxiety. That is, the present invention provides a composition comprising a hop oxidation-reaction product for the treatment, prevention, or improvement of depression and/or anxiety, and an agent comprising a hop oxidation-reaction product for the treatment, prevention, or improvement of depression and/or anxiety.

The composition and agent according to the present invention can be provided in the form of, for example, a pharmaceutical product (for example, a pharmaceutical composition), a quasi-drug, a food product, a feed product (including pet food), and can be achieved as described below.

A hop oxidation-reaction product, which is an active ingredient of the present invention, can be administered orally to human and non-human animals. Oral drugs include granules, powders, tablets (including sugar-coated tablets), pills, capsules, syrups, emulsions, and suspensions. These formulations can be formulated using pharmaceutically acceptable carriers, according to procedures commonly used in the art. Examples of the pharmaceutically acceptable carriers include, for example, excipients, binders, diluents, additives, flavoring agents, buffers, thickeners, coloring agents, stabilizing agents, emulsifiers, dispersing agents, suspending agents, preservatives, and the like.

When a hop oxidation-reaction product, which is an active ingredient of the present invention, is provided as a food product, the hop oxidation-reaction product may be directly provided as a food product or be provided as a mixture with another food. The thus provided food product is a food product containing an effective amount of the hop oxidation-reaction product. In this specification, the phrase "containing an effective amount" of the hop oxidation-reaction product refers to the content of the hop oxidation-reaction product (preferably, the S-fraction) in each food product which allows ingestion of the hop oxidation-reaction product in an amount within the range described below when the food product is taken in such an amount that the food product is usually eaten by individuals. Moreover, the term "food product" is used to refer inclusively to health foods, functional foods, food supplements, dietary supplements, health-promoting foods (for example, foods for specified health uses, functional nutritional foods, foods with function claims), and foods for special dietary use (for example, foods for infants, foods for pregnant women, foods for diseased people). When a hop oxidation-reaction product, which is an active ingredient of the present invention, is provided to animals other than human, the food according to the present invention is, of course, used as a feed.

The composition, agent, and hop oxidation-reaction product according to the present invention have an effect to prevent deterioration of mental function and thus may be provided as a mixture with a daily consumed food product, particularly a food product consumed as a dietary supplement. In this case, a predetermined amount of the composition, agent, and hop oxidation-reaction product according to the present invention may be provided in a single unit package for a single ingestion. Examples of the single unit package for a single ingestion includes packages configured to define a specific amount of material, such as carton, packaging container, can, bottle and the like. To better elicit the various effects of the composition, agent, and hop oxidation-reaction product according to the present invention, the amount of them provided for a single ingestion can be determined based on the amount of the hop oxidation-reaction product provided for a single ingestion as mentioned below. The food product of the present invention may be provided with a package label describing the information related to the ingestion amount, or be provided together with a document or the like with the information.

As mentioned above, the food product of the present invention can be provided as a mixture of a hop oxidation-reaction product with a daily consumed food product or a food product consumed as a dietary supplements, and a hop oxidation-reaction product can be mixed with a health food or a functional food, preferably a food containing one or more other components intended for the prevention of deterioration of mental function. Alternatively, one or more other components intended for the prevention of deterioration of mental function may be added to the food product of the present invention containing a hop oxidation-reaction product. The other components intended for the prevention of deterioration of mental function include those as described above.

The form of the "food product" is not specifically limited, but it may be, for example, in the form of a beverage or in a semi-liquid or gelatinous form. Moreover, the form of the dietary supplement includes tablets, which are produced by mixing and kneading a hop oxidation-reaction product in a dry powder form with, for example, excipients, a binder and the like, and compressing the mixture into tablets, and further includes capsules, which are produced by enclosing the above mixture in capsules.

The food product provided by the present invention is not specifically limited as long as it contains a hop oxidation-reaction product, which is an active ingredient of the present invention, and examples of the food product can include, but are not limited to, non-alcoholic beverages, such as soft drink, carbonated drink, fruit juice beverage, vegetable juice beverage, fruit and vegetable juice beverage, milk, soybean milk, milk beverage, drinkable yoghurt, drinkable jelly, coffee, hot chocolate, tea drink, nutritional beverage, energy drink, sports drink, mineral water, flavored water, non-alcoholic beer-taste beverage and the like; carbohydrate-containing foods and drinks, such as cooked rice, noodles, breads, pasta and the like; various types of confections including, for example, Western confections such as cookies, cakes, chocolate and the like, Japanese confections such as manju buns, yokan jelly and the like, candies, gums, cooled or frozen sweets such as yoghurt, jelly, custard pudding and the like, and snack foods; alcoholic beverages, such as whisky, bourbon whisky, spirits, liqueur, wine, fruit wine, Japanese sake, Chinese liquor, Japanese shochu, beer, non-alcoholic beer containing not more than 1% alcohol by volume, sparkling liquor, other miscellaneous liquors, white liquor highball and the like; processed foods (including delicacies) using eggs, fishes, or animal meats (including giblets and entrails such as liver and the like); processed foods, such as soups and the like; liquid diets, such as thick liquid diet and the like. Mineral water includes both carbonated and non-carbonated water.

Tea drink includes all fermented, semi-fermented, and non-fermented tea drinks, including, for example, black tea, green tea, barley tea, green tea with roasted brown rice, green leaf tea, Gyokuro green tea, roasted green tea, Oolong tea, turmeric herbal tea, Pu'er tea, rooibos tea, rose tea, chrysanthemum tea, ginkgo leaf tea, and herbal tea (for example, mint tea and jasmine tea).

Examples of fruits that are used in fruit juice beverages and fruit and vegetable juice beverages include apple, orange, grape, banana, pear, peach, mango fruit, acai berry, blue berry, and plum. Moreover, examples of vegetables that are used in vegetable juice beverages and fruit and vegetable juice beverages include tomato, carrot, celery, pumpkin, cucumber, and water melon.

The hop oxidation-reaction product, which is an active ingredient of the present invention, uses a component derived from hop, which humans have taken as a food for long years, and thus has a low toxicity, which allows safe use of the hop oxidation-reaction product on mammals in need thereof (such as, for example, human, mouse, rat, rabbit, dog, cat, cow, horse, pig, monkey and the like). The amount of the hop oxidation-reaction product to be ingested or administered can be determined depending on, for example, the gender, age and body weight of a recipient, conditions, administration time, dosage form, route of administration, other agents to be combined and the like. In the present invention, an example amount of the hop oxidation-reaction product (on the dry-mass basis) provided to an adult for a single ingestion or administration is in the range from 0.5 to 16000 mg (preferably 0.5 to 8000 mg, more preferably 0.5 to 4000 mg), and an example amount of the S-fraction (on the dry-mass basis) provided to an adult for a single ingestion or administer is in the range from 0.1 to 2000 mg (preferably 0.1 to 1000 mg, more preferably 0.1 to 500 mg, particularly preferably 0.2 to 100 mg). The above ingestion amount of the hop oxidation-reaction product, which is an active ingredient of the present invention, and the following ingestion timing and ingestion period for the hop oxidation-reaction product apply to uses for both non-therapeutic and therapeutic purposes, and the term "ingestion" (feeding) can be replaced with the term "administration" in the case of therapeutic use.

The hop oxidation-reaction product may be divided into several doses for ingestion or administration according to the conditions of a subject. The hop oxidation-reaction product in the above-described amount can be ingested or administered once a week or more frequently (preferably once every three days, more preferably daily) for one month (preferably 3 months, more preferably 6 months) to expect medium- and long-term effects.

Additionally, the hop oxidation-reaction product can be ingested by or administered to a subject before and/or after an event that causes deterioration of mental function. The number of ingestion or administration can be once or more times, preferably 3 or more times, 4 or more times, 5 or more times, or 6 or more times, either before or after the causative event. Examples of the event that causes deterioration of mental function include stress and chronic fatigue.

The composition, agent, and food product according to the present invention may be labeled as having an effect to prevent deterioration of mental function. In this case, the label for the composition, agent, and food product according to the present invention may contain some or all of the following claims for users' easy understanding. Of course, in the present invention, the phrase "suppression of deterioration of mental function" is used to refer inclusively the following indications:

for those who suffer from anxiety
for those who tend to easily lose motivation
for those who worry about loss in willingness, motivation, or spirit
for those who tend to easily feel dejected
for those who want to be forward-looking.

The present invention provides a method of suppressing deterioration of mental function, which comprises feeding or administering an effective amount of a hop oxidation-reaction product or a composition containing the same to a subject in need thereof. The subject which the hop oxidation-reaction product or the composition is ingested by or administered to is a mammal, including a human, and is preferably a human. The method of suppressing deterioration of mental function according to the present invention can be conducted according to the description concerning the composition and agent according to the present invention, and to the description concerning the active ingredient of the present invention.

The present invention provides a method of treating, preventing, or improving depression and/or anxiety, which comprises feeding or administering an effective amount of a hop oxidation-reaction product or a composition containing the same to a subject in need thereof. The subject which the hop oxidation-reaction product or the composition is ingested by or administered to is a mammal, including a human, and is preferably a human. The treatment, prevention, or amelioration method according to the present invention can be conducted according to the description concerning the composition and agent according to the present invention, and to the description concerning the active ingredient of the present invention.

The present invention provides use of a hop oxidation-reaction product or a composition containing the same for the production of a composition for use in suppressing deterioration of mental function or of an agent for suppressing deterioration of mental function, respectively. The present invention also provides use of a hop oxidation-reaction product or a composition containing the same for use in suppressing deterioration of mental function, or as an agent for suppressing deterioration of mental function. The present invention also provides a hop oxidation-reaction product for use in the prevention of deterioration of mental function. The use according to the present invention and the hop oxidation-reaction product according to the present invention can be achieved according to the description concerning the composition and agent according to the present invention, and to the description concerning the active ingredient of the present invention.

The present invention provides use of a hop oxidation-reaction product or a composition containing the same for the production of a composition for treating, preventing, or improving depression and/or anxiety or of an agent for treating, preventing, or improving depression and/or anxiety. The present invention also provides use of a hop oxidation-reaction product or a composition containing the same for treating, preventing, or improving depression and/or anxiety, or as an agent for treating, preventing, or improving depression and/or anxiety. The present invention also provides a hop oxidation-reaction product for use in the treatment, prevention, or improvement of depression and/or anxiety. The use according to the present invention and the hop oxidation-reaction product according to the present invention can be achieved according to the description concerning the composition and agent according to the present invention, and to the description concerning the active ingredient of the present invention.

The method according to the present invention and the use according to the present invention may be use in mammals including human, and are intended for both therapeutic and non-therapeutic uses. In this specification, the term "non-therapeutic" means excluding the act of performing surgery on, treating, or diagnosing a human (i.e., medical practices on humans) and specifically means excluding a procedure in which a physician or an individual who is directed by a physician performs surgery on, treats, or diagnoses a human.

EXAMPLES

The present invention will be specifically described by way of examples below, but the present invention is not limited to these examples.

Reference Example 1: Preparation of Hop Pellet Oxidation-Reaction Product

A hop pellet oxidation-reaction product was made from Hallertau Perle hops (HPE variety) in the form of a pellet. The hops were ground in a mill, and a reaction was allowed to proceed by heating at 80° C. for 24 hours. The obtained product was subjected to the following pre-analysis treatment and then to HPLC analysis.

[Pre-Analysis Treatment of Product]

Ethanol was added to the collected product to a concentration of 10% (w/v), and the resulting mixture was subjected to extraction at 50° C. for 1 hour. The obtained liquid extract was diluted 10 times with ethanol.

[Components of HPLC Apparatus]

Pump: LC-10ADvp×3 (SHIMADZU)

Degasser: DGU-20A5 (SHIMADZU)

System controller: CBM-20A (SHIMADZU)

Autosampler: SIL-20ACHT (SHIMADZU)

Column oven: CTO-20AC (SHIMADZU)

Photodiode array detector: SPD-M20A (SHIMADZU)

Waveform analysis software: LCSolution (SHIMADZU)

[HPLC Conditions]

Column: Alltima C18 2.1 mm I.D.×100 mm, particle size: 3 µm

Flow rate: 0.6 mL/min

Elution solvent A: water/phosphoric acid, 1000/0.2 (v/v), +0.02% (w/v) EDTA (free)

Elution solvent B: acetonitrile

Elution solvent C: water

Injection volume: 3 µL

Column temperature: 40° C.

Detection wavelength: 270 nm (oxidation-reaction product, iso-α-acids, α-acids, β-acids)

Gradient program:

TABLE 1

| Time (min) | Composition of mobile phase (%) | | |
|---|---|---|---|
| | A | B | C |
| 0 | 90 | 10 | 0 |
| 26.67 | 48 | 52 | 0 |
| 30 | 25 | 75 | 0 |
| 32.67 | 15 | 85 | 0 |
| 37.67 | 15 | 85 | 0 |
| 37.68 | 0 | 10 | 90 |
| 41.3 | 0 | 10 | 90 |
| 41.31 | 90 | 10 | 0 |
| 51 | | stop | |

(Washing and equilibration steps started after the time point of 37.68 min.)

(Washing and equilibration steps started after the time point of 37.68 min.)

The above product was analyzed under the above analytical conditions to calculate the ratios (%) of the values of peak areas corresponding to α-acids, β-acids, iso-α-acids to the sum of the values of all the peak areas (mAU·min), where those peaks were detected at a detection wavelength of 270 nm. Areas corresponding to solvent peaks and a negative peak caused by injection shock were excluded from the subject areas of the waveform analysis. The HPLC chromatogram of the above product obtained by the analysis was as shown in FIG. 1.

Example 1: Preparation of Hop Oxidation-Reaction Product (1) Hop Oxidation Step

Hallertau Perle hops (HPE variety) were ground in a mill, and the obtained ground hops were heated with stirring at 60° C. for about 120 hours in air. Water was added to the obtained heated hops (matured hop pellets) to give a solid concentration of 5% (w/v), and the resulting mixture was subjected to extraction at 50° C. for 30 minutes. The obtained liquid extract was separated into solid and liquid phases by decantation to obtain a solids-free liquid (with Brix value of about 2).

(2) Activated Charcoal Treatment Step

To the solids-free liquid obtained in the above step (1), activated charcoal (Y180C, manufactured by Ajinomoto Fine-chemical; at 0.5% (w/v) relative to the solids-free liquid) and polyvinylpolypyrrolidone (Polyclar 10, manufactured by ISP Japan; at 0.4% (w/v) relative to the solids-free liquid) were added, and the resulting mixture was left to stand for 2 hours. The obtained liquid mixture was supplemented with a filter aid (diatom earth) and then filtered to obtain a filtrate (with Brix value of about 1.5). The obtained filtrate was used in the following examples as an aqueous extract of the hop oxidation-reaction product.

(3) Analysis of Components in Hop Oxidation-Reaction Product

HPLC-MSMS analysis was performed on the filtrate obtained in the above step (2) (aqueous extract of the hop oxidation-reaction product) under the following conditions to measure the contents of various components in the hop oxidation-reaction product. It is known that scorpio-humulinol A, scorpio-cohumulinol A, tricyclooxyisohumulone A, and tricyclooxyisocohumulone A are contained as oxidation products of α-acids, iso-α-acids, or β-acids in a hop oxidation-reaction product (Biosci. Biotechnol. Biochem., 2015 (79): 1684-1694; J., Agric. Food Chem., 2015: 63: 10181-10191). Moreover, a standard used in the analysis was prepared in accordance with the method described in J., Agric. Food Chem., 2015: 63: 10181-10191 and J. Nat. Prod., 2014, 77, 1252-1261.

[HPLC Conditions]
Column: Unison UK-C18 100×2 mm i.d., particle size: 3 μm
Flow rate: 0.25 mL/min
Column temperature: 40° C.
Mobile Phase A: 1% formic acid in water
Mobile Phase B: 1% formic acid in acetonitrile
Injection volume: 3 μL
Gradient: From 0 to 30 min, 15 to 31% B
   From 30 to 40 min, 31 to 80% B
   From 40 to 43 min, 80% B
   Followed by washing and equilibration steps.

[MSMS Conditions]
Mass spectrometer: AB SCIEX 4000Q Trap
Ion source: ESI-negative ion mode
Ion spray voltage: −4500 V
Analytical parameters:

TABLE 2

Analytical Parameters for Each Compound

| Compound | Q1 mass (amu) | Q3 mass (amu) | Declustering potential (V) | Collision energy (V) | Cell exit potential (V) |
|---|---|---|---|---|---|
| Scorpio-humulinol A | 392.91 | 194.90 | −100 | −38 | −13 |
| Scorpio-cohumulinol A | 378.91 | 180.90 | −100 | −38 | −13 |
| Tricyclooxy-isohumulone A | 376.90 | 124.80 | −115 | −50 | −19 |
| Tricyclooxy-isocohumulone A | 362.90 | 110.80 | −60 | −50 | −17 |

The above steps (1) and (2) were repeated three times to obtain filtrates, and the contents of scorpio-humulinol A, scorpio-cohumulinol A, tricyclooxyisohumulone A, and tricyclooxyisocohumulone A in the filtrates were measured. As a result, the ratios of the total amount of tricyclooxyisohumulone A and tricyclooxyisocohumulone A to the total amount of scorpio-humulinol A and scorpio-cohumulinol A ([tricyclooxyisohumulone A+tricyclooxyisocohumulone A]/[scorpio-humulinol A+scorpio-cohumulinol A]) were as described below:

Lot 1, 3.2;
Lot 2, 6.8;
Lot 3, 12.1.

Consequently, it was found that the ratio of the total amount of tricyclooxyisohumulone and tricyclooxyisocohumulone to the total amount of scorpio-humulinol and scorpio-cohumulinol was from about 2 to 20 in the hop oxidation-reaction product.

Figure 2:
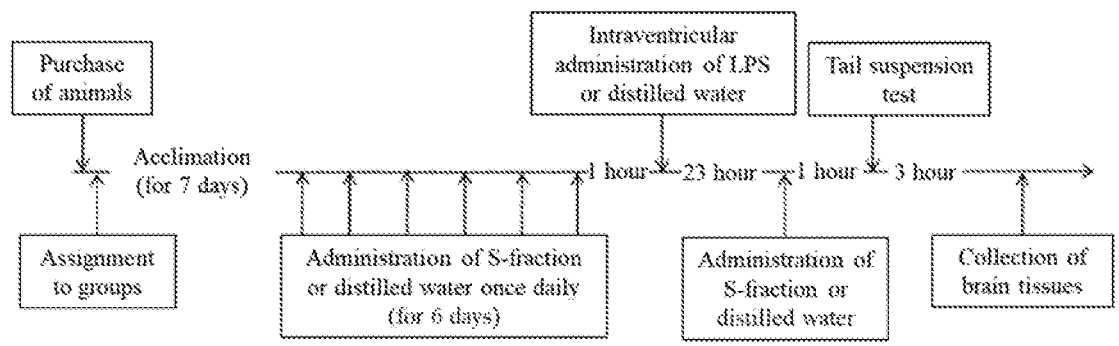
FIG. 2 is a figure showing the outline of a test in Example 2.

Example 2: Effect of Hop Oxidation-Reaction Product on Depression Condition and Loss in Willingness (1) Outline of Test A dried product from the aqueous extract of the hop oxidation-reaction product obtained in the step (2) of Example 1 (containing the S-Fr) was used as a test substance. The effect of the test substance to improve depression and to improve loss in willingness/motivation was assessed by administering mice with the test substance, then with lipopolysaccharide (LPS) to induce brain inflammation, and again with the test substance, and then subjecting the resulting mice to a tail suspension test. Additionally, brain tissues were collected from the mice after the tail suspension test, and the amount of an inflammatory cytokine was measured in the brain tissues to evaluate the brain inflammation. The outline of the test is as shown in FIG. 2.

(2) Administration of a Hop Oxidation-Reaction Product (S-Fr) (I)

Five-week-old male ICR (CD-1) mice (Charles River Laboratories Japan) were allocated into five groups of equal average body weight as indicated in Table 3. After one week of acclimation, the hop oxidation-reaction product was administered as the S-Fr to mice in the "S-Fr-1 mg administration group," "S-Fr-10 mg administration group," and "S-Fr-50 mg administration group" by oral gavage at a dose of 1, 10, or 50 mg on the dry-mass basis per kg of body weight. The administered hop oxidation-reaction product containing the S-Fr was prepared immediately prior to administration by adding distilled water to the dried aqueous extract of the hop oxidation-reaction product obtained in the step (2) of Example 1. Specifically, each aqueous solution of the S-Fr was prepared by adding a required volume of distilled water whereby the aqueous solution was administered at a dose of 10 mL/kg body weight, and the resulting aqueous solution was administered to the mice once daily by oral gavage for 6 consecutive days. In addition, the dilution solvent (distilled water) was administered to mice in the "control group" (inflammation-uninduced group) and the "S-Fr non-administration group" once daily by oral gavage at a dose of 10 mL/kg body weight for 6 consecutive days. The doses of the S-Fr administered to the mice, namely 1, 10, and 50 mg/kg body weight, are converted to equivalent doses of 5, 49, and 243 mg, respectively, for human (with a body weight of 60 kg) based on the body surface area according to the FDA guideline 2005 (Guidance for Industry Estimating the Maximum Safe Starting Dose in Initial Clinical Trials for Therapeutics in Adult Healthy Volunteers, URL: https://www.fda.gov/downloads/drugs/guidances/ucm078932.pdf).

TABLE 3

Test Groups and Administration Doses of a Hop Oxidation-Reaction Product (S-Fr)

| Test Groups | | Administration Doses of S-Fr (mg/kg body weight) |
|---|---|---|
| Control group (inflammation-uninduced group) (n = 12) | | 0 (administered only with distilled water) |
| S-Fr non-administration group (n = 11) | | 0 (administered only with distilled water) |
| S-Fr administration groups | S-Fr-1 mg administration group (n = 11) | 1 |
| | S-Fr-10 mg administration group (n = 12) | 10 |
| | S-Fr-50 mg administration group (n = 12) | 50 |

(3) Induction of Brain Inflammation

An aqueous solution of LPS with a concentration of 1.5 mg/mL was prepared by dissolving LPS (manufactured by Sigma-Aldrich Co. LLC.) in distilled water. The aqueous LPS solution was administered intraventricularly to mice in the test groups (the S-Fr non-administration group and the S-Fr administration groups) at a dose of 0.5 mg of LPS per mouse 1 hour after the administration of the S-Fr or distilled water on the 6th day from the start of the S-Fr administration. Additionally, distilled water was administered intraventricularly to mice in the control group (inflammation-uninduced group) at a dose of 10 μL per mouse.

(4) Administration of a Hop Oxidation-Reaction Product (S-Fr) (II)

After 23 hours from the administration of LPS or distilled water as described in the above step (3), the S-Fr or distilled water was administered to mice in each group by oral gavage at any of the doses indicated in Table 3.

(5) Measurement of Body Weight

The body weight of each mouse in each group was measured on the day before the tail suspension test (corresponding to an age of about 7 weeks). The results of the measurement (mean±standard deviation) were 35.0±0.7 g in the control group (inflammation-uninduced group), 34.4±0.5 g in the S-Fr non-administration group, 35.9±0.7 g in the S-Fr-1 mg administration group, 35.0±0.6 g in the S-Fr-10 mg administration group, and 34.5±0.5 g in the S-Fr-50 mg administration group, and no deviation was observed in body weight between the groups.

(6) Tail Suspension Test

After 1 hour from the administration of the S-Fr or distilled water as described in the above step (4), a tail suspension test was performed. Specifically, each of the mice was suspended upside down (tail suspension) for 6 minutes in an individual cage with an illuminance of 60 lux and a temperature of 23.5±1° C., where a 2-cm-long portion from one end of a tape (width: 1 cm, length: 15 cm) was attached to the tail of the mouse (at the position 1 cm from the tip of the tail) by winding the tape around the tail and the other end of the tape was attached to the top of the cage to lift the head of the mouse to a height of 45 to 50 cm above the bottom of the cage. The mouse held by tail suspension was visually observed from another room by using a video camera and a monitor, to measure the period of immobility (immobility time; sec) in the 6 minutes. The immobility state is defined as when a mouse stops any movement of limbs and relaxes its muscles.

The tail suspension test was developed as a method to evaluate depression-related behaviors (Cryan J F, el al. Neurosci Biobehav Rev. 2005; 29: 571-625). When a mouse is suspended upside down by the tail, the immobility state (a suspended state without any movement) subsequent to escape behaviors is observed. Thus, the time spent immobile within a certain period of time is evaluated as one of the depression-related behaviors. The immobility state observed in the tail suspension test is believed to represent a state of hopelessness in the test animal, in which the animal abandons an attempt to escape from the environment surrounding the animal, namely loss of escape willingness, and works as a willingness index. In fact, it is known that existing antidepressants with clinically proven efficacy reduce the LPS-induced immobility (Park et al. Journal of Neuroinflammation 2011, 8:12).

(7) Evaluation of Brain Inflammation

At 3 hours after the completion of the tail suspension test, the mice in each group were euthanized to collect hippocampi and cerebral cortices. Then, the amount of an inflammatory cytokine in hippocampus and cerebral cortex was measured. Specifically, each of the collected hippocampi and cerebral cortices was bead-disrupted in the RIPA buffer (manufactured by Wako Pure Chemical Industries) to measure the amount of interleukin-1β (IL-1β), a member of inflammatory cytokines, by using the Mouse IL-1β ELISA Ready-SET-Go! ELISA kit (manufactured by eBioscience). The determined value of the concentration of IL-1β was divided by the value of the concentration of total proteins in the disrupted tissue suspension that was determined by the BCA method (bicinchoninic acid method) using the BCA Protein Assay kit (manufactured by Thermo Fisher Scientific), to evaluate the content of IL-1β per unit protein mass in hippocampus or cerebral cortex.

(8) Results

Figure 3:
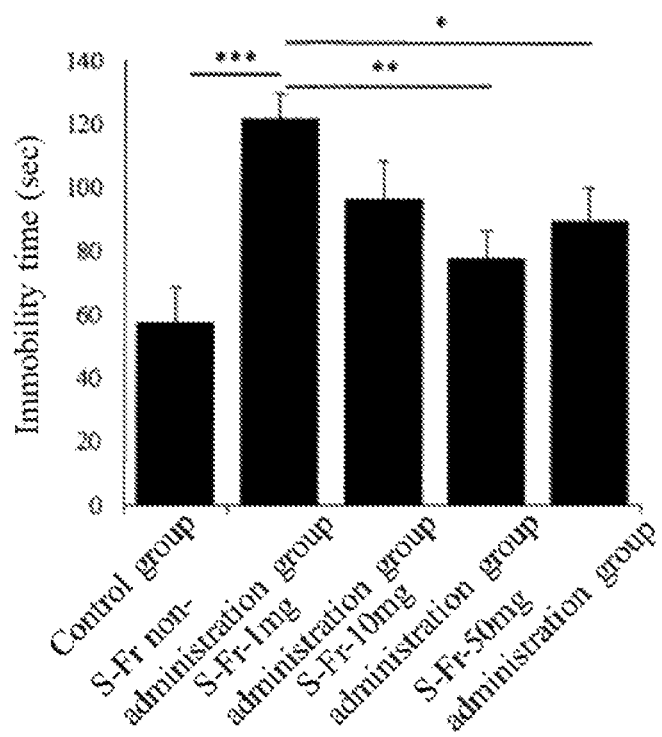
FIG. 3 is a graph depicting the period of immobility (immobility time) in control and test groups in a tail suspension test. A single asterisk (*) means $P<0.05$, and a double asterisk () means $P<0.01$, and a triple asterisk (*) means $P<0.001$.
Figure 4:
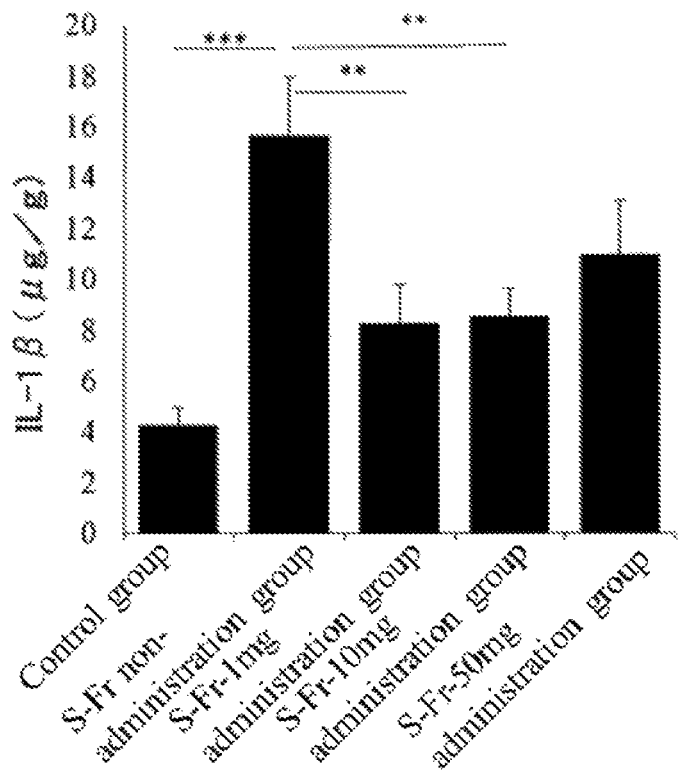
FIG. 4 is a graph depicting the amount of an inflammatory cytokine (IL-1β) in hippocampus tissues collected from the control and test groups. A double asterisk () means $P<0.01$, and a triple asterisk (*) means $P<0.001$.
Figure 5:
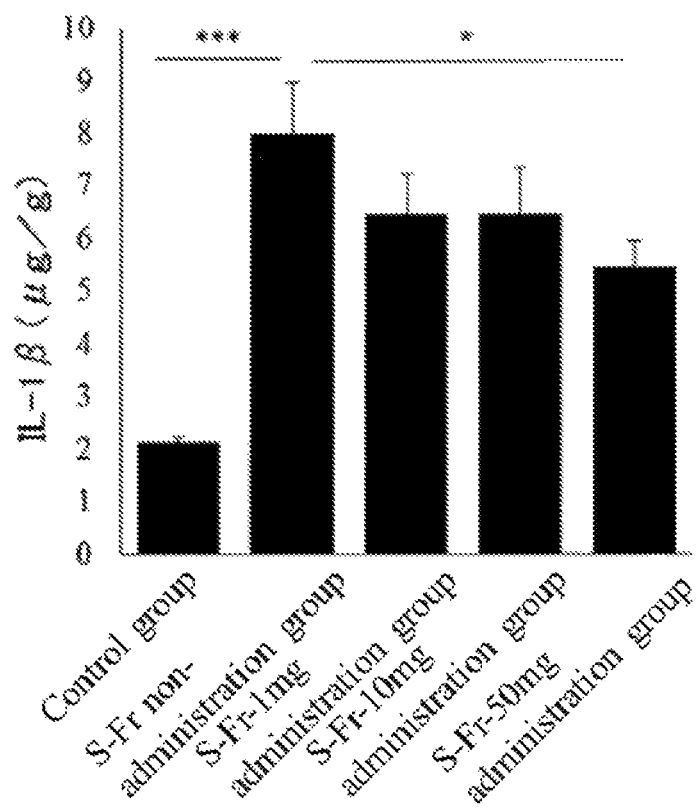
FIG. 5 is a graph depicting the amount of an inflammatory cytokine (IL-1β) in cerebral cortices collected from the control and test groups. A single asterisk (*) means $P<0.05$, and a triple asterisk (***) means $P<0.001$.

The results of the tail suspension test and the brain inflammation evaluation are as shown in FIGS. 3 to 5. Dunnett's test was used in all the tests for comparison with the S-Fr non-administration group as a control.

As shown in FIG. 3, the length of immobility time in the tail suspension test was significantly increased in the S-Fr non-administration group with induction of inflammation, compared to that in the control group (inflammation-uninduced group). In contrast, the S-Fr administration groups were observed to have a tendency to decrease the length of immobility time when compared to the S-Fr non-administration group; in particular, it was found that the length of immobility time was significantly decreased in the S-Fr-10 mg administration group and the S-Fr-50 mg administration group. This confirmed that the administration of the S-Fr resulted in improvement of a depression condition and loss in willingness and a decrease in the length of immobility time.

Additionally, as shown in FIGS. 4 and 5, the amount of IL-1β was significantly increased in the hippocampi and cerebral cortices from the S-Fr non-administration group with induction of inflammation, compared to that from the control group (inflammation-uninduced group). In contrast, the S-Fr administration groups were observed to have a tendency to decrease the amount of IL-1β when compared to the S-Fr non-administration group; in particular, it was found that the amount of IL-1β was significantly decreased in the hippocampi from the S-Fr-1 mg administration group and the S-Fr-10 mg administration group (FIG. 4), and in the cerebral cortices from the S-Fr-50 mg administration group (FIG. 5). These results indicated that administration of the S-Fr succeeded in alleviating brain inflammation, which led to the improvement of a depression condition and the improvement of loss in willingness and motivation (spirit).

Example 3: Effects of Hop Oxidation-Reaction Product on a Mood State and a Mental State (1) Outline of Test A human study to evaluate the effects of a hop oxidation-reaction product on mental functions (in particular, a mood state and a mental state) was performed. This study was a randomized, double-blinded, placebo-controlled parallel group-comparison study. The study period was 12 weeks, during which a trial diet or a control diet was provided to participants. Specifically, "a hop oxidation-reaction product-containing capsule" as a trial diet or "a hop oxidation-reaction product-free capsule" as a control diet was consumed by male and female healthy subjects with an age of 45 or more to 64 or less years, and the effects of a hop oxidation-reaction product (in particular, S-Fr) on a mood state and a mental state were evaluated in the subjects.

(2) Test Subjects

Subjects who judged by a physician to be healthy on the basis of a pre-study physical examination were randomly allocated to a trial diet group (n=30) and a control diet group (n=30). The number of subjects qualified for analysis was 27 (13 males and 14 females) in the trial diet group and was 30 (14 males and 16 females) in the control diet group, while the age of subjects qualified for analysis (mean±standard deviation) was 54.6±5.4 years in the trial diet group and was 55.4±5.3 years in the control diet group. The test subjects were allowed to maintain the same lifestyle as before the enrollment in the study.

(3) Test Diets

During the study period (12 weeks), the test subjects in the trial diet group and in the control diet group consumed 3 capsules of the trial diet and 3 capsules of the control diet, respectively, with cold or warm water once daily on a daily basis. As the trial diet, "the hop oxidation-reaction product-containing capsule" (three of the capsules contain a total of 35 mg of the S-Fr on the dry-mass basis) was used. As the control diet, "the hop oxidation-reaction product-free capsule," which had been produced in the same manner except that dextrin (Pinedex #100; manufactured by Matsutani Chemical Industry) was added instead of the S-Fr, was used. The composition of the trial diet per capsule is as shown in Table 4.

TABLE 4

Composition of Test Diets (per capsule)

| | Trial diet | | Control diet | |
|---|---|---|---|---|
| Ingredients | Mass (mg) | Blending ratio (%) | Mass (mg) | Blending ratio (%) |
| S-fraction (powder) | 69 | 19.7 | 0 | 0 |
| Dextrin (Pinedex #100) | 112 | 32.0 | 181 | 51.7 |
| Dextrin (MAX1000) | 69 | 19.7 | 69 | 19.7 |
| Gelatin capsule (#1, brown) | 100 | 28.6 | 100 | 28.6 |
| Total | 350 | 100 | 350 | 100 |

* The dried aqueous extract of the hop oxidation-reaction product obtained in the step (2) of Example 1 (containing the S-Fr) was used as the "S-fraction (powder)."

(4) Measurement

A. Measurement Item

As a measurement item, the following test was performed:

Profile of Mood States 2nd Edition (short version)(sometimes herein referred to as "POMS2 test").

B. Measurement Period

POMS2 test was performed once on the test subjects at each visit before, 6 weeks after, and 12 weeks after the onset of ingestion of either of the test diets. At the weeks 6 and 12, the test diets were consumed roughly 30 minutes before the measurement.

C. Measurement Method

POMS2 test was performed as follows. That is, the test subjects answered a total of 35 questions about the mood state which each subject was aware of in the past one week. The scores from the answers were sorted into seven subscales, including "anger-hostility," "confusion-bewilderment," "depression-dejection," "fatigue-inertia," "tension-anxiety," "vigor-activity," and "friendliness," and then the seven subscales and the "total mood disturbance" score was calculated, whereby the mood state in the past one week was evaluated. The raw score of each subscale was translated to a T-score (a value standardized on the basis of a normal distribution with a certain generation mean of 50 and a standard deviation of 10), and the resulting T-score was used for the evaluation.

(5) Evaluation and Analysis

Each subscale of the mood state was evaluated by the POMS2 test to give a score (measured value) at each measuring time point, and each of the obtained scores was subtracted with the score obtained prior to beginning of the consumption in the corresponding subscale to calculate the amount of change. The measured values and amount of change in both the groups were tested by two-sample t-test.

(6) Results

The results were as shown in Table 5.

TABLE 5

POMS2 Test Results

| Test Items | Numeric Items | Groups | Prior to beginning of the study (Week 0) | At Week 6 after beginning of the study | At Week 12 after beginning of the study |
|---|---|---|---|---|---|
| Anger-Hostility | Measured value | Control diet | 45.8 ± 8.4 | 48.0 ± 9.4 | 45.6 ± 6.4 |
| | | Trial diet | 44.3 ± 6.2 | 44.9 ± 8.0 | 44.8 ± 6.5 |
| | Amount of change | Control diet | | 2.2 ± 6.9 | −0.1 ± 7.6 |
| | | Trial diet | | 0.6 ± 7.3 | 0.5 ± 5.9 |
| Confusion-Bewilderment | Measured value | Control diet | 49.3 ± 7.4 | 49.3 ± 9.1 | 48.4 ± 8.3 |
| | | Trial diet | 50.4 ± 10.8 | 46.5 ± 8.9 | 47.3 ± 6.8 |
| | Amount of change | Control diet | | 0.0 ± 8.6 | −0.8 ± 7.6 |
| | | Trial diet | | −4.0 ± 6.6† | −3.1 ± 8.8 |
| Depression-Dejection | Measured value | Control diet | 46.8 ± 5.2 | 47.6 ± 10.0 | 46.6 ± 6.0 |
| | | Trial diet | 46.8 ± 5.8 | 45.9 ± 7.9 | 45.7 ± 4.9 |
| | Amount of change | Control diet | | 0.8 ± 7.7 | −0.2 ± 3.6 |
| | | Trial diet | | −0.9 ± 7.1 | −1.1 ± 5.0 |
| Fatigue-Inertia | Measured value | Control diet | 43.9 ± 5.4 | 45.9 ± 8.4 | 44.9 ± 6.9 |
| | | Trial diet | 46.0 ± 7.6 | 44.8 ± 8.1 | 45.7 ± 7.6 |
| | Amount of change | Control diet | | 2.1 ± 6.7 | 1.1 ± 7.9 |
| | | Trial diet | | −1.2 ± 6.2† | −0.3 ± 6.3 |

TABLE 5-continued

POMS2 Test Results

| Test Items | Numeric Items | Groups | Prior to beginning of the study (Week 0) | At Week 6 after beginning of the study | At Week 12 after beginning of the study |
|---|---|---|---|---|---|
| Tension-Anxiety | Measured value | Control diet | 48.6 ± 7.7 | 49.5 ± 9.1 | 49.2 ± 9.3 |
| | | Trial diet | 47.6 ± 10.3 | 46.0 ± 9.9 | 44.7 ± 7.0# |
| | Amount of change | Control diet | | 0.9 ± 8.5 | 0.7 ± 9.6 |
| | | Trial diet | | −1.6 ± 7.7 | −2.9 ± 8.0 |
| Vigor-Activity | Measured value | Control diet | 52.0 ± 8.6 | 50.4 ± 9.9 | 51.2 ± 9.8 |
| | | Trial diet | 49.1 ± 11.9 | 49.7 ± 10.9 | 51.6 ± 12.4 |
| | Amount of change | Control diet | | −1.7 ± 8.6 | −0.8 ± 8.5 |
| | | Trial diet | | 0.6 ± 6.8 | 2.4 ± 7.2 |
| Friendliness | Measured value | Control diet | 52.9 ± 9.3 | 51.1 ± 8.1 | 49.9 ± 8.3 |
| | | Trial diet | 51.4 ± 10.6 | 50.0 ± 8.6 | 50.4 ± 10.2 |
| | Amount of change | Control diet | | −1.8 ± 9.9 | −3.0 ± 7.6 |
| | | Trial diet | | −1.4 ± 6.7 | −1.0 ± 6.7 |
| Total mood disturbance | Measured value | Control diet | 45.9 ± 6.3 | 47.6 ± 9.4 | 46.2 ± 7.1 |
| | | Trial diet | 46.8 ± 8.4 | 45.2 ± 9.2 | 45.0 ± 7.0 |
| | Amount of change | Control diet | | 1.6 ± 6.8 | 0.2 ± 6.0 |
| | | Trial diet | | −1.6 ± 6.4† | −1.9 ± 5.7 |

Each score is calculated as mean ± standard deviation.
Comparison between groups:
P < 0.05;
†P < 0.1 (two-sample t-test).

In respect of the item "tension-anxiety," only the trial diet group showed a tendency to improve the measured values and amount of change at both 6 weeks and 12 weeks after beginning of the consumption, and a significant difference in the change of measured value was observed between both the groups at 12 weeks after beginning of the consumption (P<0.05).

In respect of the items "confusion-bewilderment," "depression-dejection," "fatigue-inertia," and "total mood disturbance," only the trial diet group showed a tendency to improve the measured values and amount of change at both 6 weeks and 12 weeks after beginning of the consumption. In addition, the amount of change in those items, except for the item "depression-dejection," tended to be significantly improved at 6 weeks after beginning of the consumption in the trial diet consumption group, as compared with the control diet consumption group (P<0.1).

In the POMS2 test, a smaller measured value means a better state in each of the items "anger-hostility," "confusion-bewilderment," "depression-dejection," "fatigue-inertia," "tension-anxiety," and "total mood disturbance," and a larger measured value means a better state in each of the items "vigor-activity" and "friendliness." Thus, in this test, a smaller change means a bigger improvement in each of the items "anger-hostility," "confusion-bewilderment," "depression-dejection," "fatigue-inertia," "tension-anxiety," and "total mood disturbance," as compared to the state prior to beginning of the consumption; and a larger change means a bigger improvement in each of the items "vigor-activity" and "friendliness," as compared to the state prior to beginning of the consumption.

The above results demonstrated that consumption of the hop oxidation-reaction product-containing capsule by the test subjects resulted in improvement (with a significant difference) of the item "tension-anxiety" in the POMS2 test, which is a mood and mental state evaluation test, and furthermore in improvement (with a tendency of a significant difference) of the items "confusion-bewilderment," "fatigue-inertia," and "total mood disturbance," and indicated that the hop oxidation-reaction product (in particular, S-Fr) had an improving effect on a mood state and a mental state.

The invention claimed is:

1. A method of suppressing deterioration of mental function, which comprises feeding or administering an effective amount of a hop oxidation-reaction product or a composition containing the same to a subject in need thereof,
   wherein the deterioration of mental function is depression in which IL-1β is involved, or loss in willingness or motivation in which IL-1β is involved,
   wherein said hop oxidation-reaction product comprises an extract obtained by oxidizing hops at a temperature of 60° C. to 100° C., and subjecting said oxidized hops to water extraction at a temperature of 50° C. to 60° C., and
   wherein said hop oxidation-reaction product has a ratio of the total amount of tricyclooxyisohumulone A and tricyclooxyisocohumulone A to the total amount of scorpiohumulinol A and scorpio-cohumulinol A from about 2 to 20.

2. The method according to claim 1, wherein the hop oxidation-reaction product or the composition containing the same is ingested by or administered to a subject with said deterioration of mental function or with a risk of said deterioration of mental function.

3. The method according to claim 1, wherein said deterioration of mental function is caused by stress or chronic fatigue.

4. The method according to claim 1, wherein the composition is a food composition.

5. The method according to claim 1, wherein the composition is in a single unit package suitable for a single ingestion.

* * * * *